United States Patent [19]

Gastgeb et al.

[11] Patent Number: 4,870,868
[45] Date of Patent: Oct. 3, 1989

[54] VIBRATION SENSING APPARATUS

[75] Inventors: Raymond F. Gastgeb, Doylestown; Edward Tom, Philadelphia, both of Pa.

[73] Assignee: Pennwalt Corporation, Philadelphia, Pa.

[21] Appl. No.: 186,843

[22] Filed: Apr. 27, 1988

[51] Int. Cl.[4] .............................................. G01N 29/00
[52] U.S. Cl. ..................................... 73/649; 273/29 A
[58] Field of Search ................. 73/649, 657, 570, 579; 273/26 R, 26 B, 26 C, 29 A, 35 R, 183 D, 184 R, 186 R, 181 G

[56] References Cited

U.S. PATENT DOCUMENTS

| 3,395,571 | 8/1968 | Murdoch | 73/67.2 |
| 3,969,927 | 7/1976 | Yoshida et al. | 73/71.4 |
| 4,090,707 | 5/1978 | Saar | 273/29 A |
| 4,101,132 | 7/1978 | Conrey et al. | 273/29 A |
| 4,141,549 | 2/1979 | Hayes et al. | 273/29 A |
| 4,212,193 | 7/1980 | Turley | 73/65 |
| 4,257,594 | 3/1981 | Conrey et al. | 273/29 A |
| 4,471,958 | 9/1984 | Piche | 273/29 A |
| 4,488,873 | 12/1984 | Bloomfield et al. | 433/71 |
| 4,519,245 | 5/1985 | Evans | 73/579 |
| 4,599,898 | 7/1986 | Beer | 73/579 |

FOREIGN PATENT DOCUMENTS 3414467 1/1985 Fed. Rep. of Germany .

Primary Examiner—Tom Noland
Assistant Examiner—Louis M. Arana
Attorney, Agent, or Firm—Bernard F. Plantz

[57] ABSTRACT

A sensing device is disclosed which produces a response when the point of impact between an object and a member occurs at a preselected location on the member. When the member vibrates after being impacted by the object, an oscillatory electrical signal is produced by a piezoelectric sensor. Appropriate circuitry is provided for analyzing the oscillatory electrical signal and for producing a response if the object impacted the member at the preselected location. The sensing apparatus is particularly useful in athletics for determining whether a game object contacted the athletic instrument at its "sweet spot".

21 Claims, 3 Drawing Sheets

VIBRATION SENSING APPARATUS

BACKGROUND OF THE INVENTION

The present invention relates to a vibration sensing apparatus and, more particularly, to a device for indicating the location of the point of impact between an object and a member.

When an object impacts a member or vice versa, it is often desirable to determine the location of the point of impact on the member. For example, many sports require a player to strike a ball or other game object with a hand held athletic instrument, such as a bat, racket, or club. The player's success in the sport is often determined by his or her ability to swing the athletic instrument so that a preferred portion of the instrument collides with the game object. This preferred portion of the athletic instrument is generally referred to as the "sweet spot".

Athletic instruments which are hand held and designed to strike a game object contain two vibrational nodes. The first node is located under the player's hands, while the second node is located at the "sweet spot". When the game object impacts the instrument at the "sweet spot", a maximum amount of energy is transferred to the game object with a minimum amount of vibration generated within the instrument. However, if the point of impact occurs at a location other than at the vibrational node or "sweet spot", a damped vibration is generated within the instrument. This damped vibration absorbs much of the energy which was to be transferred to the game object. Thus, the game object is not propelled from the athletic instrument at an optimum velocity. It is therefore advantageous for the player to develop good eye-hand coordination so that the athletic instrument imparts the game object at the "sweet spot".

Sensing devices have been attached to athletic instruments for detecting whether the game object contacts a preselected location on the instrument. R. N. Conrey et al. in U.S. Pat. Nos. 4,101,132 and 4,257,594 disclose an athletic instrument, such as a tennis racket, with electronic sensors for detecting contact or proximity of the game element at a preselected location within the intended contact area. Specifically, optoelectrical sensors, resistance or capacitance change sensors, capacitive phase angle change sensors, piezoelectric or piezoresistive sensors, ambient light change sensors, reflected light sensors and electro-fiber optical sensors are employed to determine when the ball contacts the "sweet spot" of a tennis racket. Circuitry is provided which is responsive to the output from the sensor for providing an audible or audio-visual response when the ball contacts the "sweet spot".

The sensing equipment described by Conrey et al. requires the athletic instrument to be specially retrofitted with the electronic sensors. If optical sensors are employed, they are attached and properly aligned on the racket frame so that when the ball contacts the "sweet spot", the beam of light is broken. The optical sensor is either mounted within a hole formed in the racket frame or attached to the frame with tape which contains conductor paths. The conductor paths are used to electrically connect the sensor to the appropriate circuitry. When piezoelectric or piezoresistive elements are used, they are wound around the racket strings within the "sweet spot". If the ball strikes the strings in close proximity to these elements, the stress induced in the elements produces either a voltage or resistance change. The change in voltage or resistance is monitored with voltage or resistance measuring circuits. These circuits generate a logic "yes" when the characteristics change by a predetermined amount. The logic "yes" then activates a switch which controls a means for producing a response which indicates contact was made with the "sweet spot".

It would be desirable to have a sensing device which could be removably attached to a conventional racket, golf club, baseball bat or the like and avoid the need for a specially designed athletic instrument requiring the placement of sensors in or around the intended contact area. Furthermore, it would be desirable to have a sensing device which could be easily transferred to be used on a variety of different athletic instruments to determine whether the player is making contact with the "sweet spot".

SUMMARY OF THE INVENTION

The sensing apparatus of the present invention determines and indicates when the point of impact between an object and a member occurs at a preselected location on the member. The sensing apparatus includes a piezoelectric sensor for producing an oscillatory electrical signal which is proportional to the vibration in the member generated by the collision between the object and the member. A circuit is also provided which is responsive to the oscillatory electrical signal for producing a control signal when the amplitude and frequency of the electrical signal correspond to a point of impact at said preselected location. An indicating means, responsive to the control signal, is also included for indicating that the point of impact occurred at the preselected location.

DETAILED DESCRIPTION OF THE PREFERRED EMBODIMENTS

Figure 1:
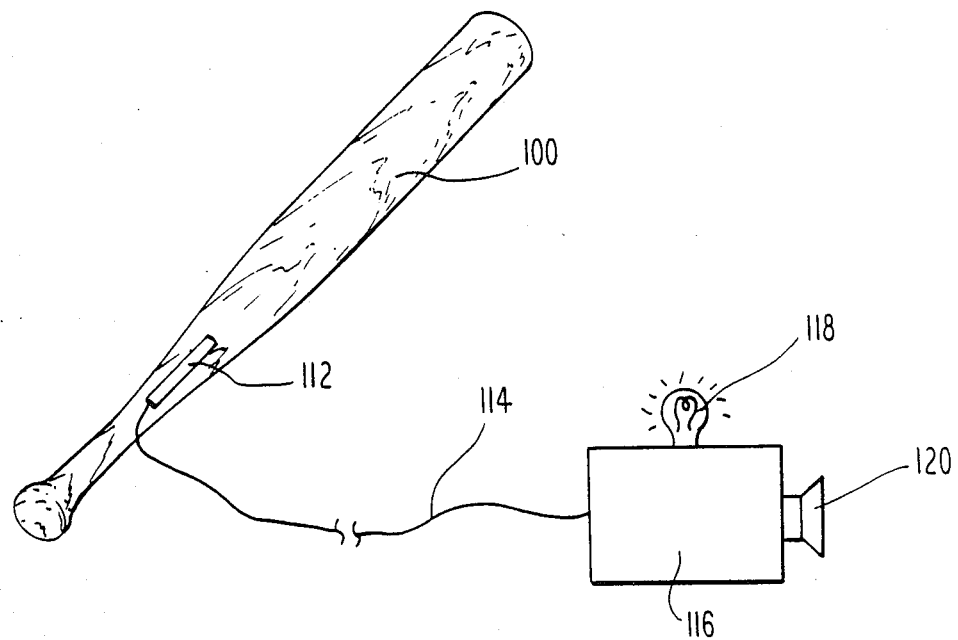
FIG. 1 illustrates the first embodiment of the present invention where the sensing apparatus is attached to a baseball bat.

Referring now to FIG. 1, the sensing apparatus of the present invention will be described in conjunction with its use on a baseball bat 100. When a baseball contacts the bat 100, vibrations are transmitted throughout the bat. The piezoelectric sensor 112 attached to the bat 100 produces an oscillatory electrical signal which has both an amplitude and frequency which are proportional to these vibrations. This oscillatory electrical signal is then transmitted via the cable 114 to the housing 116 which contains the circuitry and the indicatingn means which produce a response when the point of impact on the bat is at the preselected location. The housing 116 contains a lamp 118 and a speaker 120 for producing an audio-visual response. Alternatively, either the lamp 118 or the speaker 120 may be eliminated so that only a visual or audio response is produced. Although the housing 116 is shown as being remotely located from the bat 100, the components located with the housing may be mounted on or within the bat, such as in a bore formed in the handle of the bat.

The present invention provides two alternative modes of operation. In the first mode, a response is produced by the indicating means when the ball strikes a vibrational node or "sweet spot" of the bat. This mode of operation serves as a positive response stimuli indicating that the ball and bat are colliding at an optimum location. In the second mode of operation, a response is produced by the indicating means when the ball strikes a location other than a vibrational node or "sweet spot" of the bat. The second mode indicates that the ball and bat are not colliding at an optimum location. The housing 116 will contain a switching mechanism (not shown) which allows the player to select the desired mode of operation.

The location of the "sweet spot" or vibrational node of the bat depends on the physical characteristics of the bat, the hand location, and the grip strength of the player grasping the bat. However, since the sensing apparatus of the present invention only analyzes the vibrational pattern within the bat, the piezoelectric sensor 112 can be attached to any portion of the bat regardless of the grip strength or hand location of the player. However, it is particularly advantageous to attach the sensor 112 to a location which is remote from the intended impact area between the bat 100 and the ball. The placement of the sensor at the remote location ensures that sensor will not interfere with the bat's contact with the ball.

The piezoelectric sensor used in the present invention is a flexible, piezoelectric polymer film, such as polyvinylidene fluoride (PVDF), with electrodes formed thereon. The electrodes are typically electroconductive layers, such as a thin film metal or a conductive polymer, which are applied to opposing sides of the piezoelectric polymer film. Polyvinylidene fluoride is approximately 50% crystalline and 50% amorphous. The principal crystalline forms of PVDF are the highly polar $\beta$ form and the nonpolar $\alpha$ form. High piezoelectric response is associated with the polar $\beta$ form. In order to increase the piezoelectric properties of polyvinylidene fluoride, the film is mechanically oriented and subjected to an intense electrical field, otherwise known as poling, to cause the oriented $\beta$ form crystallites to predominate. The piezoelectric polymer films used in the present invention are typically oriented $d_{31}$. Piezoelectric polymer films which have been treated in this manner are available from the Pennwalt Corporation, Philadelphia, PA, under the trademark KYNAR. Other suitable piezoelectric polymers useful in the present invention include copolymers of vinylidene fluoride and tetrafluoroethylene ($VF_2$–$VF_4$), and copolymers of vinylidene fluoride and trifluoroethylene ($VF_2$–$VF_3$).

As is conventionally known, when piezoelectric polymer films are flexed, such that the film is put in compression and/or tension, a voltage is produced due to the change in the surface charge density of the polymeric material. When vibrations are transmitted to the film, such as when the ball contacts the bat, the repeated flexure of the piezoelectric film caused by the vibrations produces an oscillatory voltage output.

Figure 2:
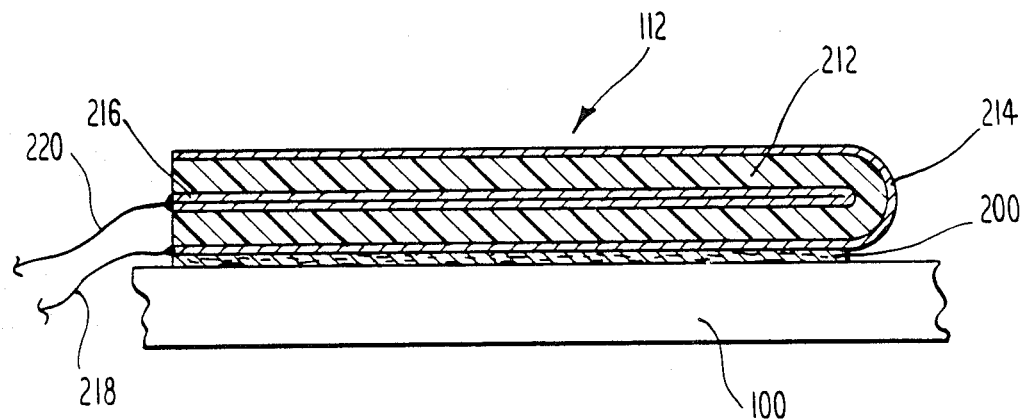
FIG. 2 is a partial side view of the baseball bat shown in FIG. 1 illustrating the attachment of the piezoelectric sensor to the bat.

Referring now to FIG. 2, the attachment of the piezoelectric sensor 112 to the bat 100 is shown. In the present invention, it is advantageous to attach the piezoelectric sensor 112 in a manner such that it can be easily removed when the player does not want to utilize the sensing device. However, it should understood that the piezoelectric sensor 112 could be permanently affixed to the bat 100 or other athletic instrument. The piezoelectric sensor 112 is a piezoelectric polymer film 212 with opposed, metallized surfaces 214 and 216. The metallization material is typically silver ink or a sputtered metal film. This piezoelectric polymer film 212 is then folded in the manner shown such that the metallized surface 216 is put in a face-to-face relationship. The folded metallized surface is typically glued together with a suitable adhesive, such as cyano acrylate, epoxy or the like. The bottom portion of the other metallized surface 214 is then attached to the baseball bat 100 with double-sided tape 200 or other suitable adhesives, such as 3M 6065 spray adhesive. The cable 114 shown in FIG. 1 consists of two separate strands of conductors 218 and 220. The conductors 218 and 220 are attached to the metallized surfaces 214 and 216, respectively, with rivets, conductive tape or conductive epoxy. The piezoelectric sensor 112 may also be a metallized piezoelectric polymer film in an unfolded configuration.

Figure 3:
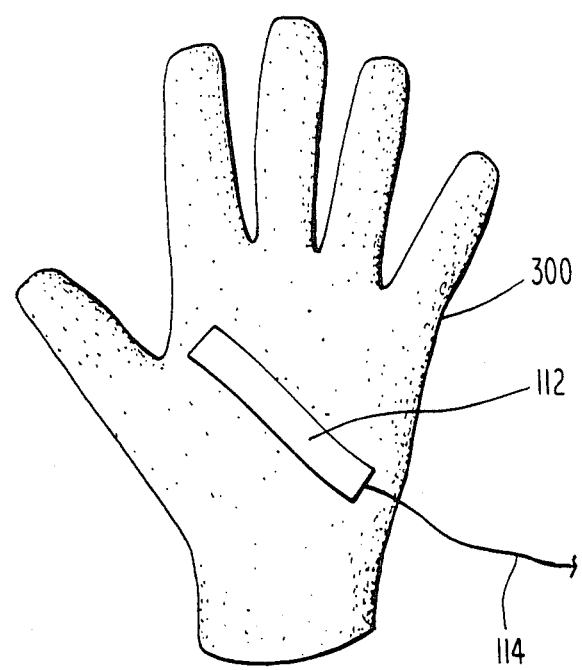
FIG. 3 illustrates an alternative embodiment of the present invention wherein the piezoelectric sensor is attached to a glove.

Referring now to FIG. 3, an alternative embodiment of the present invention will be described. In this embodiment, the piezoelectric sensor 112 is attached to a glove 300, such as a baseball batter's glove or a golf glove. When the player wearing this glove grips a baseball bat or golf club, the piezoelectric sensor 112 is put in intimate contact with the bat or club. Thus, when vibrations are produced in the instrument by the ball contact, these vibrations are transferred to the piezoelectric sensor which generates the oscillatory electrical signal. As in the first embodiment of the present invention shown in FIG. 1, the oscillatory electrical signal is then transmitted to the appropriate electrical circuitry by a cable 114. The piezoelectric sensor 112 may be positioned within the palm of the glove, as shown in FIG. 1, or it may be positioned on the fingers of the glove so that the sensor contacts the bat when grasped by the player.

Figure 4A:
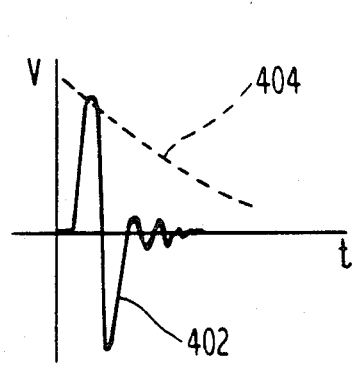
FIG. 4a is a graph of voltage versus time for the oscillatory electrical signal which is produced when the object collides with a vibrational node of the member.
Figure 4B:
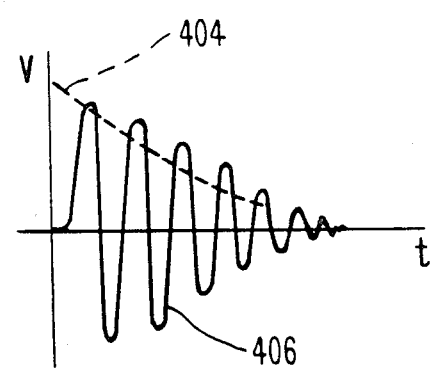
FIG. 4b is a graph of voltage versus time for the oscillatory electrical signal when the object collides with the member at a location other than at a vibrational node of the member.

FIGS. 4a and 4b are graphs of the oscillatory electrical signals which are produced when a ball collides with the bat. FIG. 4a illustrates an oscillatory electrical signal 402 which is produced when the ball contacts the bat at a vibrational node. As shown in the figure, after the sharp initial peak, the signal dissipates because the subsequent vibrations within the bat have a very small amplitude. The dotted line 404 illustrates the voltage characteristics of a discharging capacitor. The electrical circuitry of the present invention compares the oscillatory electrical signal to this discharging capacitor. If the first mode of operation has been selected, after the initial peak caused by the ball contacting the bat, the circuit analyzes the oscillatory electrical signal from the piezoelectric film to determine if any subsequent vibrations have an amplitude which is greater than the voltage of the discharging capacitor at that point in time. If the voltage of the oscillatory electrical signal after the initial spike is less than the voltage of the discharging capacitor, the circuit recognizes that the ball contacted the "sweet spot" or vibrational node, and a response is generated by the indicating means.

Turning now to FIG. 4b, the oscillatory electrical signal 406 generated when the ball contacts a point other than the vibrational node is shown. This signal is damped because of the amplitude of the vibrations which are produced after the ball initially contacts the bat. Again, this signal 406 is compared to the voltage output of the discharging capacitor illustrated by the dotted line 404. However, the second peak of the oscillatory electrical signal has an amplitude which is greater than the voltage of the discharging capacitor. If the second mode of operation has been selected, the electrical circuitry of the present invention produces a control signal which is supplied to the indicating means for generating a response which signifies that a point other than the vibrational node of the bat has been contacted by the ball.

Figure 5:
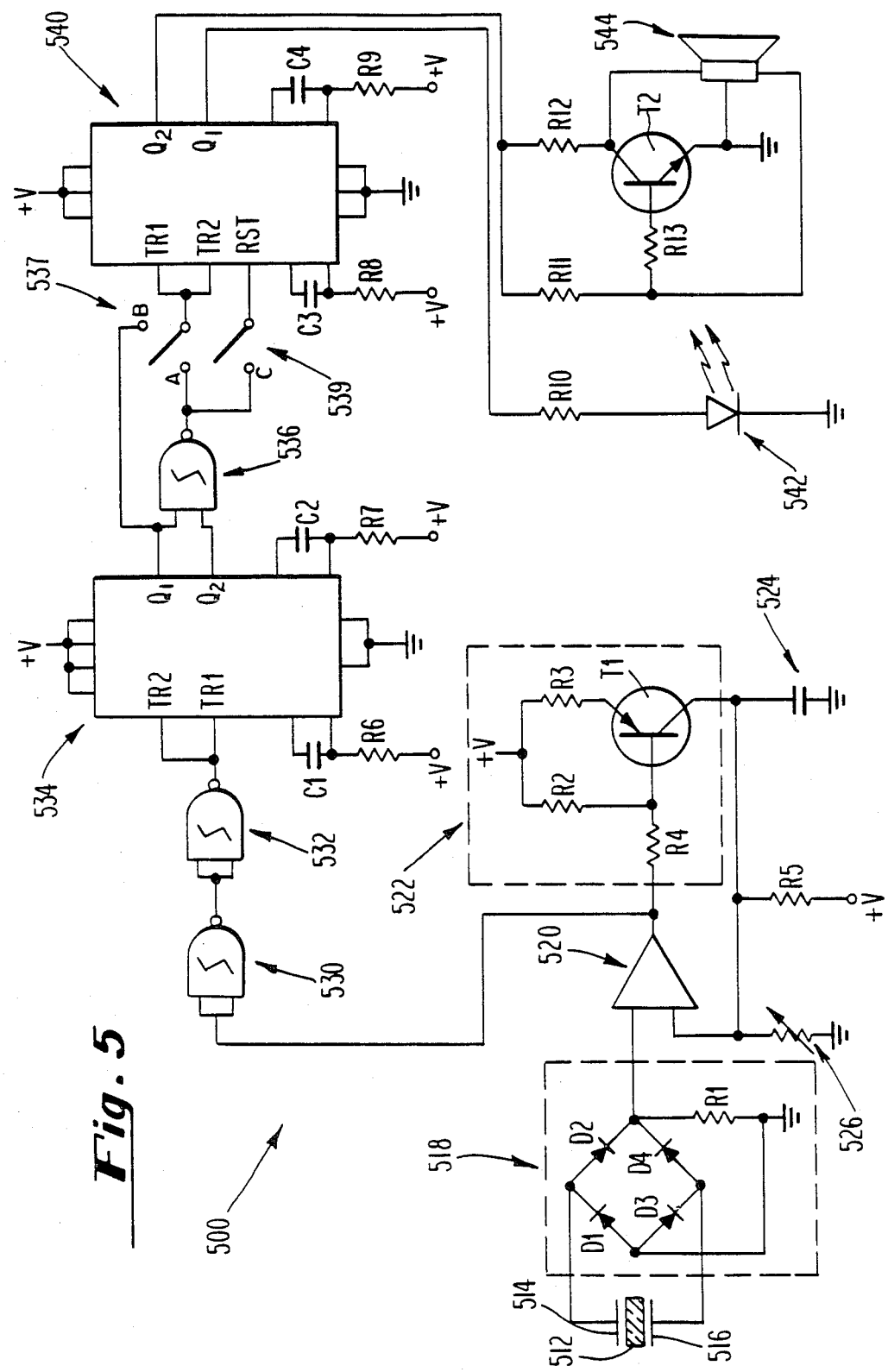
FIG. 5 is an electrical schematic of the circuit means and indicating means used in the present invention for producing a response when the point of impact between the object and member occurs at a preselected location on the member.

Referring now to FIG. 5, the schematic of the circuit means and indicating means used in the present invention is generally designated as 500. The piezoelectric polymer film 512 with its opposed metallized surfaces 514 and 516 is electrically connected to a full wave rectifier 518. The schematic illustrates that the full wave rectifier 518 is composed of diodes D1, D2, D3, and D4 along with resistor R1. The rectified signal is then supplied to an operational amplifier 520 which functions as the comparing means in the present invention.

A means 522 for charging and discharging the capacitor 524 is shown by the dotted line. The charging and discharging means 522 contains a voltage source, resistors R2, R3 and R4, and a PNP transistor T1. The output from the transistor T1 is supplied to the capacitor 524 which when discharging is used as a reference signal which is compared to the rectified oscillatory electrical signal produced by the piezoelectric polymer film 512. The capacitor 524 is also electrically connected to a voltage source through the resistor R5 and a potentiometer 526. The potentiometer 526 is used to adjust the voltage output of the discharging capacitor 524. This adjustment allows for the present invention to be calibrated when it is applied to different athletic instruments. Calibration is necessary because the amplitude of the oscillatory electrical signal will vary between instruments because of the differences in geometry and construction materials.

The output signal from the operational amplifier 520 is also supplied to a pair of Schmidt triggers 530 and 532 which are connected in series. The output of the Schmidt trigger 532 is connected to two one-shots 534, such as CD4528 available from RCA Corporation. Capacitors, C1 and C2, and resistors, R6 and R7, are connected to the two one-shots 534. The output from the two one-shots 534 is then supplied to the Schmidt trigger 536. A pair of switches 537 and 539 are positioned between the two one-shots 534 and the two one-shots 540. These switches 537 and 539 are used to select the desired mode of operation.

The two one-shots 540 are connected to capacitors, C3 and C4, and resistors R8 and R9. The output from the two one-shots 540 is the control signal which is supplied to the indicating means which produces a response to indicate that the ball has contacted the bat at the preselected location. A visual response is produced by the light emitting diode 542 which is connected through a resistor R10 to the two one-shots 540. An audio response is produced by the speaker 544 which is electrically connected with the resistors R11, R12 and R13, and an NPN transistor T2. Although FIG. 5 illustrates that an audio-visual response is produced, it may be desirable to eliminate either the light emitting diode 542 or the speaker 544 so only a visual or audio response is produced.

In the first mode of operation, where a response is produced only when the ball contacts a vibrational node or "sweet spot" of the bat, the switch 537 is set to contact the B terminal while the switch 539 is closed to contact the C terminal. When the first spike of the oscillatory electrical signal from the piezoelectric sensor 512 is supplied to the operational amplifier 520, the logic state of the output of the amplifier 520 changes from one to zero. The charging means 522 charges the capacitor 524 and then starts to discharge the capacitor 524 when the logic state of the output of the amplifier 520 changes. The changing logic state of the amplifier 520 also triggers the timers, $Q_1$ and $Q_2$, of the two one-shots 534. The $Q_2$ timer changes from logic zero to logic one and then back to logic zero before the $Q_1$ timer changes from logic zero to logic one.

When the second peak of the oscillatory electrical signal is supplied to the operational amplifier 520, its voltage is compared to the voltage of the discharging capacitor 524 at that point in time. As shown in FIG. 4b, when the ball contacts a location other than the "sweet spot" or vibrational node of the bat, the voltage of the discharging capacitor is less than the voltage of the second spike of the oscillatory electrical signal. When this condition exists, the logic state of the output of the amplifier 520 again changes from zero to one causing the $Q_2$ trigger of the two one-shots 534 to change to logic one. If the logic state change in $Q_2$ occurs while $Q_1$ is at logic one, the reset pin RST on the two one-shots 540 is activated to prevent a control signal from being supplied to the light emitting diode 542 and speaker 544. Thus, a response is not produced by the indicating means.

As shown in FIG. 4a, if the voltage of the discharging capacitor is greater than the voltage of the second spike of the oscillatory electrical signal, a control signal will be supplied from the two one-shots 540 to the light emitting diode 542 and the speaker 544 to indicate that the "sweet spot" has been hit. The operational amplifier does not change its logic state because the capacitor voltage is greater than the voltage of the second spike. Thus, the $Q_2$ trigger is not activated on the two one-shots 534. Since the $Q_1$ trigger on the two one-shots 534 is still at its logic one state as a result of the first spike, the triggers TR1 and TR2 of the two one-shots 540 are activated to emit the control signal from $Q_1$ and $Q_2$ of the two one-shots 540.

In the second mode of operation, where a response is produced only when the ball contacts a location other than a vibrational node or "sweet spot" of the bat, the switch 537 contacts the A terminal while the switch 539 is open. When the first spike of the oscillatory electrical signal from the piezoelectric sensor 512 is supplied to the operational amplifier 520, the logic state of the output from the amplifier 520 changes from one to zero. This change in logic state causes the charging means 522 to charge and then discharge the capacitor 524. The changing logic state of the amplifier 520 also triggers the timers, Q1 and Q2, of the two one-shots 534 to a logic one state. However, the Q2 timer returns to its zero logic state while the Q1 timer remains at a logic one state.

When the second peak of the oscillatory electrical signal is supplied to the operational amplifier 520, its voltage is compared to the voltage of the discharging capacitor 524. If the voltage of the discharging capacitor is less than the voltage of the oscillatory electrical signal, the logic state of the operational amplifier 520 again is changed to zero causing the Q2 trigger in the two one-shots 534 to change from its zero logic state to a logic one. This condition corresponds to the graph shown in FIG. 4b. If the change in the logic state of the Q2 trigger occurs while the Q1 trigger is still at the one logic state from the first spike, the triggers TR1 and TR2 of the two one-shots 540 are activated and a control signal is supplied to the light emitting diode 542 and the speaker 544 which produce a response indicating that a location other than the "sweet spot" has been contacted.

If the voltage of the discharging capacitor is greater than the voltage of the second peak of the oscillatory electrical signal, as shown in FIG. 4a, the operational amplifier 520 does not change its logic state and an output signal is not supplied to the two one-shots 534 while the Q1 trigger is at a logic one state. Therefore, the triggers, TR1 and TR2, of the two one-shots 540 are not activated and a control signal is not supplied to the light emitting diode 542 and the speaker 544.

In both modes of operation discussed above, the two one-shots 534 and 540 in conjunction with the operational amplifier 520 analyze the oscillatory electrical signal to determine if it possesses an amplitude and frequency which correspond to the ball contacting the preselected location. Specifically, the decay of the oscillatory electrical signal produced when the ball hits the bat and vibrates the piezoelectric polymer film is compared to the decay of the discharging capacitor to determine if the hit occurred on the "sweet spot" or at a location off of the "sweet spot".

Although the present invention has been described using a baseball bat, other athletic instruments, such as golf clubs, tennis rackets and the like may be used without departing from the spirit and scope of the present invention. The sensing apparatus of the present invention can also be used to analyze vibrations in a beam used as a supporting structure or vibrations in a cantilever, such as an airplane wing.

What is claimed is:

1. An apparatus for sensing and indicating when the point of impact between an object and a member occurs at a preselected location on said member, comprising:
    a piezoelectric sensor for producing an oscillatory electrical signal having an amplitude and frequency which are proportional to the vibration in said member generated by the collision between said object and said member;
    means for attaching said piezoelectric sensor to said member at a location remote from the point of impact of said member;
    circuit means responsive to said oscillatory electrical signal for producing a control signal when the amplitude and frequency of said oscillatory electrical signal correspond to a point of impact at said preselected location on said member; and
    indicating means responsive to said control signal for indicating that the point of impact on said member occurred at said preselected location.

2. An apparatus according to claim 1 wherein said circuit means further comprises:
    means for selecting whether said control signal is produced when the preselected location corresponds to a point of impact located at a vibrational node of said member or at a location other than at a vibrational node of said member.

3. An apparatus according to claim 1 wherein said indicating means generates an audio, visual or audio-visual response.

4. An apparatus according to claim 1 wherein said circuit means comprises:
    a capacitor;
    means for controlling the charging and discharging of said capacitor;
    comparing means for comparing the voltage of said oscillatory electrical signal to the voltage of said capacitor as it is discharging and for producing an output signal when the voltage of said oscillatory electrical signal is greater than the voltage of the discharging capacitor; and
    means responsive to said output signal for producing said control signal when the decay of the voltage of the discharging capacitor is greater than the decay of the voltage of said oscillatory electrical signal.

5. An apparatus according to claim 1 wherein said circuit means comprises:
    a capacitor;
    means for controlling the charging and discharging of said capacitor;
    comparing means for comparing the voltage of said oscillatory electrical signal to the voltage of said capacitor as it is discharging and for producing an output signal when the voltage of said oscillatory electrical signal is greater than the voltage of the discharging capacitor; and
    means responsive to said output signal for producing said control signal when the decay of the voltage of the discharging capacitor is less than the decay of the voltage of said oscillatory electrical signal.

6. An apparatus according to claim 1 wherein said piezoelectric sensor comprises:
    a piezoelectric polymer film having opposing sides; and
    an electroconductive layer disposed on each of the opposing sides of said film.

7. An apparatus according to claim 6 wherein said piezoelectric polymer film is folded such that the electroconductive layer on one of said opposing sides is in a face-to-face relationship.

8. An apparatus for sensing when the point of impact between a game object and a sports instrument adapted to strike said game object occurs at a preselected location on said game instrument, comprising:
    a game instrument adapted to be hand held and to strike said game object;
    a piezoelectric sensor contacting said game instrument in a location which is remote from the area where the game object collides with said game instrument, said sensor producing an oscillatory electrical signal having an amplitude and frequency which are proportional to the vibration in said game instrument generated by the collision between said game object and said game instrument;
    circuit means responsive to said oscillatory electrical signal for producing a control signal when the amplitude and frequency of said oscillatory electrical signal corresponds to a point of impact at said preselected location on said game instrument; and indicating means responsive to said control signal for indicating that the point of impact on said game instrument occurred at said preselected location.

9. An apparatus according to claim 8, further comprising:
means for attaching said piezoelectric sensor to said game instrument.

10. An apparatus according to claim 8 wherein said circuit means further comprises:
means for selecting whether said control signal is produced when the preselected location corresponds to a point of impact located at a vibrational node of said game instrument or at a location other than at a vibrational node of said game instrument.

11. An apparatus according to claim 8 wherein said piezoelectric sensor is attached to a glove so as to contact said game instrument when the user wearing said glove grasps said game instrument.

12. An apparatus according to claim 8 wherein said indicating means generates an audio, visual or audio-visual response.

13. An apparatus according to claim 8 wherein said circuit means comprises:
a capacitor;
means for controlling the charging and discharging of said capacitor;
comparing means for comparing the voltage of said oscillatory electrical signal to the voltage of said capacitor as it is discharging and for producing an output signal when the voltage of said oscillatory electrical signal is greater than the voltage of the discharging capacitor; and
means responsive to said output signal for producing said control signal when the decay of the voltage of the discharging capacitor is greater than the decay of the voltage of said oscillatory electrical signal.

14. An apparatus according to claim 8 wherein said circuit means comprises:
a capacitor;
means for controlling the charging and discharging of said capacitor;
comparing means for comparing the voltage of said oscillatory electrical signal to the voltage of said capacitor as it is discharging and for producing an output signal when the voltage of said oscillatory electrical signal is greater than the voltage of the discharging capacitor; and
means responsive to said output signal for producing said control signal when the decay of the voltage of the discharging capacitor is less than the decay of the voltage of said oscillatory electrical signal.

15. An apparatus according to claim 8 wherein said game instrument is a baseball bat.

16. An apparatus according to claim 8 wherein said game instrument is a racket.

17. An apparatus according to claim 8 wherein said game instrument is a gold club.

18. An apparatus according to claim 8 wherein said piezoelectric sensor comprises:
a piezoelectric polymer film having opposing sides; and
an electroconductive layer disposed on each of the opposing sides of said film.

19. An apparatus according to claim 18 wherein said piezoelectric polymer film is folded such that the electroconductive layer on one of said opposing sides is in a face-to-face relationship.

20. An apparatus for sensing and indicating when the point of impact between an object and a member occurs at a preselected location on said member, comprising:
a piezoelectric sensor for producing an oscillatory electrical signal having an amplitude and frequency which are proportional to the vibration in said member generated by the collision between said object and said member;
a capacitor;
means for controlling the charging and discharging of said capacitor;
comparing means for comparing the voltage of said oscillatory electrical signal to the voltage of said capacitor as it is discharging and for producing an output signal when the voltage of said oscillatory electrical signal is greater than the voltage of the discharging capacitor;
means responsive to said output signal for producing said control signal when the decay of the voltage of the discharging capacitor is greater than the decay of the voltage of said oscillatory electrical signal; and
indicating means responsive to said control signal for indicating that the point of impact on said member occurred at said preselected location.

21. An apparatus for sensing and indicating when the point of impact between an object and a member occurs at a preselected location on said member, comprising:
a piezoelectric sensor for producing an oscillatory electrical signal having an amplitude and frequency which are proportional to the vibration in said member generated by the collision between said object and said member;
a capacitor;
means for controlling the charging and discharging of said capacitor;
comparing means for comparing the voltage of said oscillatory electrical signal to the voltage of said capacitor as it is discharging and for producing an output signal when the voltage of said oscillatory electrical signal is greater than the voltage of the discharging capacitor;
means responsive to said output signal for producing said control signal when the decay of the voltage of the discharging capacitor is less than the decay of the voltage of said oscillatory electrical signal; and
indicating means responsive to said control signal for indicating that the point of impact on said member occurred at said preselected location.

* * * * *